United States Patent [19]

Nakamoto et al.

[11] 4,448,692

[45] May 15, 1984

[54] LIQUID CHROMATOGRAPH

[75] Inventors: Akira Nakamoto, Takatsuki; Katsuhiko Saito, Otsu, both of Japan

[73] Assignee: Shimadzu Corporation, Kyoto, Japan

[21] Appl. No.: 470,553

[22] Filed: Feb. 28, 1983

[30] Foreign Application Priority Data

Feb. 27, 1982 [JP] Japan .................................. 57-31411
Jun. 29, 1982 [JP] Japan ............................. 57-98345[U]

[51] Int. Cl.³ ............................................. B01D 15/08
[52] U.S. Cl. .................................... 210/656; 210/741; 210/101; 210/198.2
[58] Field of Search ..................... 210/101, 198.2, 656, 210/659, 741

[56] References Cited

U.S. PATENT DOCUMENTS 3,984,315 10/1976 Ernst et al. ........................ 210/198.2
4,043,906 8/1977 Helmer ............................. 210/198.2
4,045,343 8/1977 Achener et al. .................. 210/198.2
4,233,156 11/1980 Tsukara et al. .................. 210/198.2

Primary Examiner—John Adee
Attorney, Agent, or Firm—Walter H. Schneider

[57] ABSTRACT

A liquid chromatograph comprising a reciprocating single plunger pump having a pair of check valves; a solvent supply passage, from the outlet check valve of the pump to a column; a driver means for the plunger of the pump; a control means for controlling the velocity of the plunger; the control means comprising a pressure detecting means disposed in the solvent supply passage, a memory means for storing a pressure signal obtained from the detecting means at a predetermined point between the initiation and termination of the suction, and a comparator means for comparing the stored pressure signal with a signal indicating a pressure which is derived from the pressure detecting means; the signal produced from the comparator means allowing the velocity at which the plunger is moved for delivery from the initiation of delivery stroke until the outlet pressure of the pump reaches the pressure at the predetermined point to be controlled so that it is greater than a velocity of the plunger set for the subsequent movement for delivery.

9 Claims, 7 Drawing Figures

LIQUID CHROMATOGRAPH

BACKGROUND OF THE INVENTION

1. Field of the Invention

The present invention relates to a solvent delivery device for liquid chromatography and, more particularly, to such a device which delivers solvent to a liquid chromatography column using a plunger pump.

2. Description of the Prior Art

Although conventional plunger pumps for solvent delivery devices for use in liquid chromatography are available in various kinds, that is, reciprocating single plunger pump, double plunger pump and triple plunger pump, compressibility of solvent at higher pressure has required to compensate for the change in flow rate due to solvent compression, irrespective of the kind of plunger pump used. Specifically, a compensating rate at a certain pressure corresponding to the compressibility of a solvent used is determined first, then the compensating rate is changed in proportion to the pressure so that liquid compressibility may be a linear function of pressure. In this method, the plunger speed at a certain flow rate can be given by $$Ve' = Ve + KPVe$$

where $Ve'$ is a plunger speed at a certain pressure P; Ve is a plunger speed at P=O; K is a compensating coefficient for a specific solvent. In the above formula, KPVe is a compensating plunger speed corresponding to the compensating flow rate at a certain pressure P.

Such a flow rate compensation has required that the compensating quantity be manually adjusted whenever another solvent having a different compressibility is used.

Also, in the prior art method, the velocity at which the plunger is moved for delivery is uniformly speeded up in accordance with the increase of the pressure in the plunger pump. However, such speedup of the velocity is sometimes insufficient, while the quantity of solvent compressed in the pump chamber is also increased with the increase of the pressure. Therefor, the prior art method causes to take much time for compression of solvent, delays the operation of the outlet check valve of the pump and then increases the pulsation of the solvent delivered.

SUMMARY OF THE INVENTION

In view of these difficulties, it is an object of the present invention to provide a liquid chromatograph which comprises a reciprocating single plunger pump having a pair of check valves respectively disposed on the outlet and inlet of the pump, a solvent supply passage through which solvent is supplied from the outlet check valve of the pump to a column, a driver means for causing the plunger of the pump to move for delivering solvent and to move faster for sucking solvent, and a control means for controlling the velocity at which the plunger is moved for the delivery or suction, the control means comprising a pressure detecting means disposed in the solvent supply passage, a memory means for storing a pressure signal obtained from the detecting means at a predetermined point between the initiation and termination of the suction, and a comparator means for comparing the stored pressure signal indicating a pressure and derived from the pressure detecting means, the signal produced from the comparator means allowing the velocity at which the plunger is moved for delivery from the initiation of delivery stroke until the pressure reaches the pressure at the predetermined point to be controlled so that it is greater than a velocity of the plunger set for the subsequent movement for delivery.

That is, the chromatograph according to the invention has a control means exerting control over the velocity of the plunger of the reciprocating single plunger pump when it is moved for delivering solvent so that the velocity of the plunger immediately after the initiation of the delivery is made larger than the velocity set for the subsequent delivery until the pressure in the solvent supply passage reaches the pressure at a predetermined point immediately before the initiation of the delivery during the suction process, and automatic compressibility (flow rate) compensation is provided for various solvent. In addition, the time during which the pressure of the solvent supply passage is lowered is shortened, thus preventing pulsation at higher pressures.

DETAILED DESCRIPTION OF THE INVENTION

One preferred embodiment of the present invention is described in detail hereinafter with reference to the accompanying drawings. It is to be understood that the invention is not limited to the embodiment since various changes and modifications may be made thereto without departing from the spirit and scope of the invention.

Figure 1:
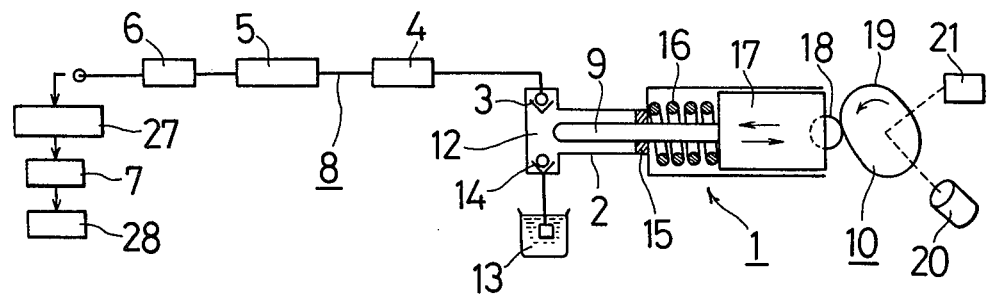
FIG. 1 illustrates the function of one example of solvent supply device for liquid chromatography according to the present invention.
Figure 2:
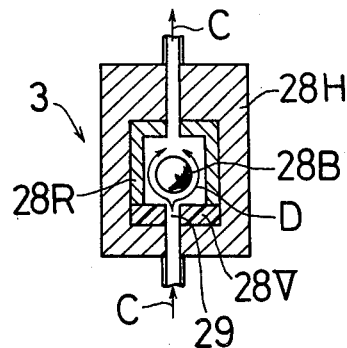
FIG. 2 is a cross-sectional view of the outlet check valve of the device shown in FIG. 1.
Figure 3:
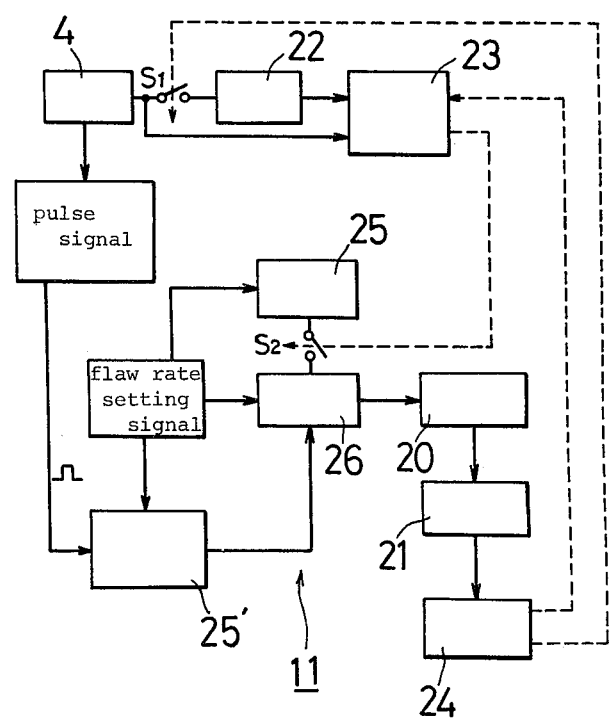
FIG. 3 illustrates the control means of the device shown in FIG. 1.
Figure 4:
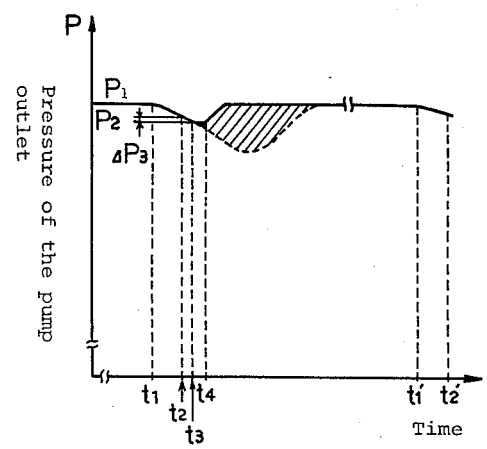
FIG. 4 is a graph showing the relationship between the pressure at the outlet of a pump and time.
Figure 5:
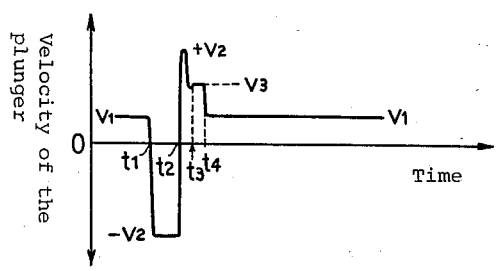
FIG. 5 is a graph showing the relationship between the velocity of the plunger of the pump and time.
Figure 6:
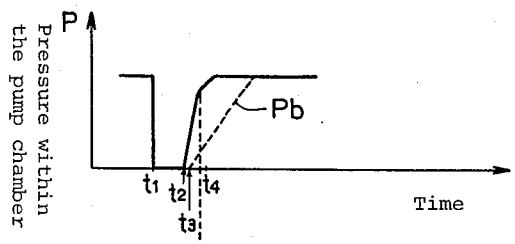
FIG. 6 is a graph showing the relationship between the pressure within the pump chamber and time.

Referring first to FIGS. 1–3, there is shown a solvent delivery device 1 for use in high-speed liquid chromatography. The device 1 is comprised of a reciprocating single plunger pump 2 having an outlet check valve 3, a solvent supply passage 8 extending from the valve 3 of the pump for supplying solvent to a column 7 through a pressure 4 disposed at the outlet of the pump, a small capacity damper 5, and a filter 6, a driver means 10 for causing the plunger 9 in the pump 2 to move for delivery and to move faster for suction, and a control means 11 for controlling the velocity of the plunger 9 when it is moved for delivery.

When the pump 2 retracts its plunger 9, solvent is sucked into its pump chamber 12 from a solvent reservoir 13 through an inlet check valve 14. On the other hand, when the pump 2 advances the plunger, solvent in the chamber 12 is delivered into the solvent supply passage 8 through the aforementioned outlet check valve 3. The pump further includes a plunger seal 15, a coil spring 16, a plunger holder 17 and a bearing 18.

The means 10 for driving the plunger comprises a special cam 19, which is rotated by a stepping motor 20 and its curved periphery is pressed into contact with the bearing 18. The cam 19 is a conventional cam and imparts a linear movement accompanying velocity change to the bearing. The rotational position of the cam 19, that is the position of the plunger 9, is detected by a photo-sensor 21.

The control means 11 comprises said pressure sensor 4, a memory circuit 22 for storing signals indicating the pressures at the outlet of the pump at the terminations of every period of the delivery and suction strokes for the plunger, a comparator circuit 23 for comparing the stored signals with the signal derived from the sensor 4 and indicating a pressure, a plunger position monitor 24 for detecting the position of the plunger by means of the photo-sensor 21 to monitor the position, specific valve setting circuits 25 and 25' for setting the specific valves according to the flow rate, a pulse generator circuit 26, switches $S_1$ and $S_2$, other various signal transmitting circuits (not shown), etc.

In addition, the solvent delivery device 1 includes an injector 27 and a LC detector 28, as for example an ultraviolet-visible spectrophotometer.

Referring specifically to FIG. 2, the check valve 3 has a ball 28B, a housing 28H, a valve chest 28R, a valve seat 28V and an opening 29.

The principal operation of the solvent delivery device 1 constructed as described above is now described. Referring next to FIGS. 1-6, when a solvent, such as methanol, acting as a mobile phase, is rapidly sucked by the plunger moving at its maximum velocity, $-V_2$, the outlet pressure P of the pump slightly decreases from pressure $P_1$ at the beginning of suction $t_1$ to pressure $P_2$ at the ending of suction $t_2$ due to the rapid suction and the action of the damper. During this process, the photo-sensor 21 disposed in association with the cam 19 detects the reference position of the plunger, and then the monitor 24 counts the number of pulses fed to the stepping motor 20 to continuously monitor the position of the plunger. The ending point of the suction $t_2$ is indicated by the monitor 24, which momentarily closes the switch $S_1$ at this instant. Thus, the signal indicative of the pressure $P_2$ and derived from the sensor 4 is stored in the memory circuit 22. At the same time, the setting circuit 25' causes the plunger 9 to be advanced at the same velocity $V_2$ as in the rapid suction during a pulse width period proportional to the pressure $P_2$, that is, from $t_2$ to $t_3$. This pulse width is set for the solvent having the lowest compressibility among the mobile phases used in liquid chromatography. This assures that solvent in the pump chamber is smoothly compressed when a delivery process is initiated. In a situation where a solvent having a large compressibility like methanol is used, the pressure in the pump chamber will not reach the stored pressure $P_2$ in that pulse width time and so the outlet check valve 3 of the pump will not open yet. Therefore, the outlet pressure of the pump P decreases further to a value satisfying the relation $$P_2 - P = \Delta P \geq 0.5 \text{ Kg/cm}^2$$

at $t_3$ and $P = P_3$, when the comparator circuit 23 causes the switch $S_2$ to close. Then, the setting circuit 25 drives the plunger 9 so that it moves at a velocity $V_3$ which is lower than the maximum velocity for the rapid suction and higher than the velocity set for delivery flow rate.

As a result, the compression of solvent in the pump chamber 12 is accelerated and the pressure P reaches the pressure $P_2$, when ($t_4$) the comparator circuit 23 causes the switch $S_2$ to open. Then the velocity is returned to the original value $V_1$, corresponding to the set delivering flow rate. These rapid suction and characteristic delivery operations are continuously repeated. It should be noted that if the resolution of the pressure sensor permits, the value of the right side of the above formula may be lower than 0.5 Kg/cm².

Next, the operation of the check valve 3 at the outlet as shown in FIG. 2 is described for reference. The valve chest 28R and the valve seat 28V are installed in the housing 28H, and when solvent is delivered, the stream of the solvent C in the direction of arrow D keeps the ball 28B apart from the seat 28V. Then, when the pump 2 turns from the delivery state to a suction state, the plunger is rapidly retracted in a time of about 0.15 second, whereby the small amount of solvent C moves fast in reverse. The result is that the ball 28B rapidly closes opening 29 of the seat 28V under the action of the viscosity of the solvent.

As described thus far, since the solvent delivery device 1 detects the pressure at the pump outlet and controls the velocity of the plunger in response thereto, no manually compressibility compensation is required. Further, as the compression of the solvent in the pump chamber is carried out rapidly, flow pulsation decreases.

It is to be noted that the aforementioned velocity $V_3$ of the plunger for compression of the solvent is changed according to the set flow rate for the following reason. Although it is preferred that the velocity $V_3$ assumes a greater value, if it is set to an excessively large value, then the difference between the velocities $V_3$ and $V_1$ becomes too great in a case of a low flow rate, for example several tens of μl/min., with the result that the motor speed cannot immediately return to the original value at point $t_4$, producing an overshoot. This makes the compensating quantity great and sometimes rather renders the flow rate too great. In particular, if the flow rate is set to 10 μl/min., the velocity $V_3$ of the plunger is preferably set to a value corresponding to 200-500 μl/min. Also, if the flow rate is set to 1 ml/min., the velocity $V_3$ is preferably set to a value corresponding to 2-3 ml/min. The decrease in the pressure in a time from $t_2$ to $t_4$ is in excess of 0.5 Kg/cm², but this period is quite short and the value 0.5 Kg/cm² is small. Further, once the outlet check valve of the pump opens, the velocity of the plunger returns to the given value. Consequently, even when the solvent is replaced by a different solvent, automatic compressibility compensation is provided, resulting in no change in the flow rate.

Figure 7:
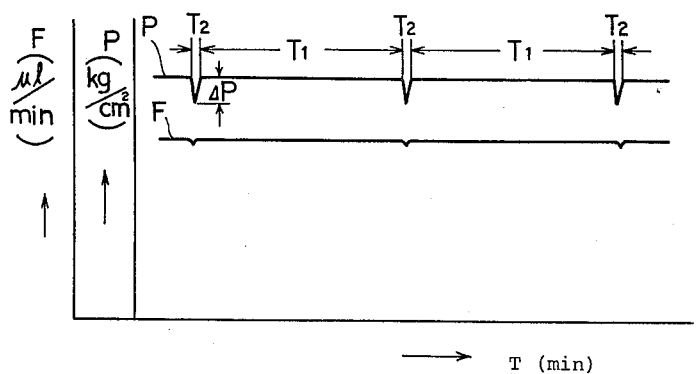
FIG. 7 is a graph showing the relationship among the pressure at the outlet of the pump, flow rate and time when the flow rate delivered by the pump is set to 10 $\mu l/min$.

FIG. 7 shows the relation among the pressure P of the pump outlet, flow rate F and time when the delivery flow rate is set to 10 μl/min. The flow rate effectively compensated by the aforementioned procedure ranges from 1 to 3,000 μl/min. When a plunger presently often used and having a capacity of about 100 μl per stroke is employed, if the set flow rate exceeds the above range, then the compensating quantity will be insufficient and will cause an error, because the maximum delivery velocity of such a plunger can reach on the order of 10 ml/min. at most. However, the flow rate range defined above is sufficient for practical applications in liquid chromatography and will not pose any problem. Also, in the above example, one stroke time taken by the rapid suction is set to about 1 second for a flow rate of 10 μl/min. and about 0.2 second for a flow rate of 100 μl/min., and it is set to 0.15 second throughout a flow rate range from that value to 9,900 μl/min., for example. In this way the period $t_2-t_1$ is very short. As an example, if a plunger frequently used and having a capacity of about 100 μl per stroke is employed and if the flow rate is set to 10 μl/min., then the time required for a delivery is about 600 seconds. It is then assumed that $t_2-t_1=1$ sec. Then, the quantity of solvent (mobile phase) needed to be supplied into the column during the rapid suction is about 0.17 μl, that can be sufficiently made up by the compressibility of the solvent in the passage as well as by the damper having a quite small capacity. As such, the decrease in the pressure $(P_1-P_2)$ during rapid suction from t2 to t1 is very small at lower flow rate range thus to introduce substantially no pressure drop.

Unlike the above embodiment, it is possible to store the pressure P1 at the initiation of suction in the memory for driving the plunger at a high velocity until the pressure of the pump outlet reaches the pressure $P_1$ at the beginning of a suction process. In this case, even when the pressure change varies the value of the flow rate slightly, especially if the setting flow rate is large, pulsation can be reduced effectively.

It is to be understood that the present invention is not limited to the foregoing description and the drawings. Note also that the passage for returning the mobile phase to the pump while no sample is injected is not shown. Further as the control circuit for the stepping motor is known and does not constitute the invention per se, it is shown schematically. In addition, the aforesaid motor may be a motor other than a stepping motor.

The solvent delivery device according to the invention will further yield the following advantages.

(1) Especially at a low flow rate range from 1 to 1,000 μl/min., even if the pressure varies within the range from 0 to 500 Kg/cm², a constant flow rate can automatically be obtained at all times, irrespective of the kind of solvent used.

(2) Especially when the flow rate ranges from several tens of μl/min. to several hundred μl/min. as encountered in a situation where a micro bore column whose inner diameter is roughly less than 1 mm, even if the pressure increases to 500 Kg/cm², for instance, the time during which the delivered flow is accompanied by pulsation can be shortend so as to be negligible in accordance with the novel method. In addition, the variation magnitude can also be reduced. Consequently, it is possible to deliver mobile phase while producing substantially no pulsation within this range. Furthermore, the compressed fluid in the passage from the pump to the column interferes with the pulsation, thereby substantially eliminating the pressure variations in delivering solvent, though it is required, of course, that the content volume of said passage be a given volume.

(3) Even when air bubbles enter the pump chamber while the plunger is being retracted, and also when air bubbles are generated in the chamber, the plunger moves fast at the beginning of a delivery stroke until a pressure stored in the memory just prior to the delivery is attained and so the bubbles are compressed rapidly, whereby the bubbles can very readily escape from the chamber even at lower flow rate range where the plunger moves at very low velocities.

What is claimed is:

1. In a liquid chromatography system comprising a reciprocating single plunger pump provided with a pump chamber communicating through an inlet valve with a solvent reservoir and through an outlet valve with a solvent supply passage, said solvent supply passage communicating with a chromatographic column and a detector; and a drive means for moving said plunger through suction and delivery strokes whereby solvent is drawn into said pump chamber from said solvent reservoir and discharged into said solvent supply passage, said drive means being adapted to provide a set velocity to said suction stroke greater than the set velocity of said delivery stroke, the improvement for controlling the velocity stroke of said pump plunger so as to compensate for the compressibility of the solvent thereby minimizing pulsating of the solvent within the chromatography system, which comprises a delivery stroke velocity control system including a pressure detecting means disposed in said solvent supply passage for measuring pump outlet solvent pressure; memory means for receiving and storing a pressure signal provided by said pressure detecting means at a predetermined point during the suction stroke of said pump plunger; comparator means associated with said memory means for measuring the pressure differential between said stored pressure signal and an outlet solvent pressure signal measured by said pressure detecting means at the initiation of the subsequent delivery stroke of said pump plunger; means for increasing the velocity of said delivery stroke in response to said pressure differential to an adjusted velocity between the set velocities of said suction and delivery strokes; means for maintaining said adjusted velocity until the outlet pressure in said solvent supply passage corresponds to said stored pressure signal; and means for establishing and maintaining the set delivery velocity for the remainder of the delivery stroke.

2. A liquid chromatograph as set forth in claim 1, wherein the solvent supply passage is provided with a pulsation damper means between the column and the pressure detecting means disposed in the passage.

3. A liquid chromatograph as set forth in claim 1, wherein the solvent supply passage is provided with a pulsation damper of a small capacity between the column and the pressure detecting means disposed in the passage.

4. In a liquid chromatography system comprising a reciprocating single plunger pump provided with a pump chamber communicating through an inlet valve with a solvent reservoir and through an outlet valve with a solvent supply passage, said solvent supply passage communicating with a chromatographic column and a detector; and a drive means for moving said plunger through suction and delivery strokes whereby solvent is drawn into said pump chamber from said solvent reservoir and discharged into said solvent supply passage; said drive means being adapted to provide a set velocity to said suction stroke greater than the set velocity of said delivery stroke, the method for controlling the velocity of the delivery stroke of said pump plunger so as to compensate for the compressibility of the solvent thereby minimizing pulsating of the solvent within the chromatography system which comprises: measuring the pump outlet solvent pressure in the solvent supply passage at a predetermined point in time during the suction stroke of the pump plunger; determining the pressure differential between said suction stroke outlet pressure and the outlet pressure measured at the initiation of the subsequent delivery stroke of said pump plunger; increasing the velocity of the delivery stroke in response to said pressure differential to an adjusted velocity between the set velocities of said suction and delivery strokes; maintaining said adjusted velocity until the outlet pressure in said solvent supply passage corresponds to said suction stroke outlet passage; and establishing and maintaining the set velocity for the remainder of the delivery stroke.

5. A liquid chromatograph as set forth in claim 4, wherein said predetermined point is the point at which the suction is terminated.

6. A liquid chromatograph as set forth in claim 4, wherein said predetermined point is the point at which the suction is initiated.

7. A liquid chromatograph as set forth in claim 4, wherein the column has an inner diameter less than 1 mm and solvent is supplied at a rate of 10-100 $\mu$l/min.

8. A liquid chromatograph as set forth in claim 7 wherein the complete suction stroke takes 0.1-0.2 second at its maximum velocity.

9. A liquid chromatography system as set forth in claim 1 in which the drive means is a stepping motor.

* * * * *